(12) United States Patent
Fischer Lokou

(10) Patent No.: US 11,051,863 B2
(45) Date of Patent: Jul. 6, 2021

(54) CURVED PLUG FOR THE FIXING OF BONE ELEMENTS

(71) Applicant: SPINE ARCH BREVET, Oberschaeffolsheim (FR)

(72) Inventor: David François Fischer Lokou, Oberschaeffolsheim (FR)

(73) Assignee: SPINE ARCH BREVET, Oberschaeffolsheim (FR)

( * ) Notice: Subject to any disclaimer, the term of this patent is extended or adjusted under 35 U.S.C. 154(b) by 3 days.

(21) Appl. No.: 16/323,303

(22) PCT Filed: Jul. 27, 2017

(86) PCT No.: PCT/EP2017/069090
§ 371 (c)(1),
(2) Date: Feb. 5, 2019

(87) PCT Pub. No.: WO2018/024614
PCT Pub. Date: Feb. 8, 2018

(65) Prior Publication Data
US 2020/0187994 A1 Jun. 18, 2020

(30) Foreign Application Priority Data

Aug. 5, 2016 (FR) ...................................... 1670437

(51) Int. Cl.
*A61F 2/44* (2006.01)
*A61B 17/70* (2006.01)
(Continued)

(52) U.S. Cl.
CPC ........ *A61B 17/7098* (2013.01); *A61F 2/4455* (2013.01); *A61B 17/1671* (2013.01); *A61B 17/8805* (2013.01)

(58) Field of Classification Search
CPC ............ A61B 17/7098; A61B 17/1671; A61B 17/8805; A61B 17/72
(Continued)

(56) References Cited

U.S. PATENT DOCUMENTS 4,790,303 A   12/1988   Steffee
6,056,749 A *   5/2000   Kuslich .............. A61B 17/1757
                                                          606/86 A
(Continued)

FOREIGN PATENT DOCUMENTS

FR     3 054 787 A1   2/2018
WO     00/67651 A1   11/2000
(Continued)

OTHER PUBLICATIONS

International Search Report (PCT/ISA/210) dated Dec. 13, 2017, by the European Patent Office as the International Searching Authority for International Application No. PCT/EP2017/069090.
(Continued)

*Primary Examiner* — Eduardo C Robert
*Assistant Examiner* — David C Comstock
(74) *Attorney, Agent, or Firm* — Buchanan Ingersoll & Rooney PC

(57) ABSTRACT

An implant can enable the fixing of at least two adjacent bone elements in a rapid, reliable and low-invasive manner. This implant includes a curved and hollow rod allowing the use of a sealing element. A method for fixing at least two adjacent bone elements implements this implant. This method can be especially suitable for the solidarization of at least two vertebrae for the realization of an arthrodesis.

13 Claims, 2 Drawing Sheets

(51) Int. Cl.
*A61B 17/88* (2006.01)
*A61B 17/16* (2006.01)

(58) Field of Classification Search
USPC ..... 623/17.11; 606/246, 254, 255, 257, 261, 606/92–94
See application file for complete search history.

(56) References Cited

U.S. PATENT DOCUMENTS

| | | | | |
|---|---|---|---|---|
| 8,298,264 | B2* | 10/2012 | Betz | A61B 17/7055 |
| | | | | 606/246 |
| 8,579,903 | B2* | 11/2013 | Carl | A61B 17/1671 |
| | | | | 606/86 R |
| 8,951,295 | B2* | 2/2015 | Matityahu | A61B 17/866 |
| | | | | 606/329 |
| 9,204,886 | B2* | 12/2015 | May | A61B 17/1642 |
| 9,888,918 | B2* | 2/2018 | Moskowitz | A61B 17/7001 |
| 10,179,014 | B1* | 1/2019 | Menmuir | A61B 17/8605 |
| 10,314,631 | B2* | 6/2019 | Gonzalez Blohm | |
| | | | | A61B 17/864 |
| 2004/0059333 | A1 | 3/2004 | Carl et al. | |
| 2004/0064058 | A1 | 4/2004 | McKay | |
| 2005/0261695 | A1 | 11/2005 | Cragg et al. | |
| 2006/0089642 | A1* | 4/2006 | Diaz | A61B 17/72 |
| | | | | 606/60 |
| 2006/0195091 | A1 | 8/2006 | McGraw et al. | |
| 2008/0065069 | A1 | 3/2008 | Betz et al. | |
| 2012/0165871 | A1 | 6/2012 | Malone | |
| 2013/0030530 | A1 | 1/2013 | Blain | |
| 2013/0144344 | A1* | 6/2013 | Giancola | A61B 17/742 |
| | | | | 606/304 |
| 2014/0277462 | A1 | 9/2014 | Yerby et al. | |

FOREIGN PATENT DOCUMENTS

| | | |
|---|---|---|
| WO | 2004/049915 A2 | 6/2004 |
| WO | 2006/088776 A2 | 8/2006 |
| WO | 2015/148964 A1 | 10/2015 |

OTHER PUBLICATIONS

Written Opinion (PCT/ISA/237) dated Dec. 13, 2017, by the European Patent Office as the International Searching Authority for International Application No. PCT/EP2017/069090.

* cited by examiner

CURVED PLUG FOR THE FIXING OF BONE ELEMENTS

The present invention provides a new implant for a surgical use allowing the fixing of at least two adjacent bone elements in a rapid, reliable and low-invasive manner. The present invention describes also a method for fixing at least two adjacent bone elements implementing this new implant. This method is particularly suitable for the solidarization of at least two vertebrae in order to make an arthrodesis; said implant is then curve-shaped what makes it particularly well adapted for spine surgery.

With regards to ageing of the population and also to the rhythm of life of the active population, the bone problems generate or are a part of the clinical picture of a lot of pathologies. In addition the traumas related to accidents, shocks and falls, could also generate problems at the bone level requiring a surgical operation. The possibility of fixing bone elements to each other in order to stabilize or to correct a given position is thus an important medical challenge. Indeed, in the field of spine surgery in particular the fact of being able to solidarize bone elements in order to stabilize given areas and/or to release compressed nerve bundles and is often the only way of relieving the patients.

In the field of the orthopaedic surgery one commonly uses plates and screws in order to stabilize adjacent bone areas or to confer to them a given position. The materials used are obviously solid and the material and the equipment impose many mechanical constraints. To allow more adaptation and to authorize more possibilities with the surgeons, different devices were implemented in order to allow a better surgical answer for each patient: surgical screws in combination with different angles, static plates, articulated plates, cages, etc.

In the particular field of spine surgery, surgeons use in general pedicle screws also called tulip screws to solidarize vertebrae. These screws of medical use are straight screws that allow arthrodesis, that is to say the bone fusion between at least two vertebrae. This technique is commonly used for fractures, scoliosis, instability and significant pain. Even if this technique is very usually practised, the installation of pedicle screws remains a difficult procedure that is reserved to the specialized surgeons and is likely to involve false ways. In the cases of false ways, one or more screws are not correctly placed, they can wound the nerve rots or have a solidity defect. To address this possibility of false way, several sophisticated systems of assistance to guidance are used by the surgeons, one will in particular quote «the navigation» including infrared detection coupled to a peroperative scanner. These navigation systems allow decreasing the risk of error of trajectory. However the error risk factor remains important because the arthrodesis practised to date require at least four pedicle screws and more often six to eight pedicle screws.

Thus the techniques used to date present several disadvantages including the complexity of the devices to implant, the transpedicle approach for the fixation screws of these devices that is relatively invasive and generator of side-effects (haemorrhage, nerve injury, etc.), the need for an follow-up implying powerful imaging techniques, all of which being risk factors, involving technicality and costs that are to be taken into account.

The presence of nerves, blood vessels and other tissues that must necessarily be preserved at the time of bone surgeries impose limited access ways and approaches to the surgeon. The errors of trajectories are all the more numerous as the access ways are difficult or exiguous. In certain cases taking into account the spatial configuration of the bone elements to solidarize the techniques known from the prior art do not offer any solution. Thus there is a real need for new technical solutions opening new possibilities of fixation of bone elements in specific configurations.

According to a first characteristic of the invention, the curved implant is one of theses solutions, and has never been suggested to date. As a matter of fact, the implant according to the invention has the advantage of allowing the installation of a solid fixing requiring only one access way. The curved shape allows as for it to work with access ways offering working angles that are not appropriate for the straight screws known from the prior art.

The present invention proposes a simple surgical implant that allows to realize the fixing of at least two adjacent bone elements, for example two adjacent vertebrae, with no risk of false way, with no particular technical difficulty and without expensive technical help other than a simple X-ray equipment. In the case of the spine surgery, contrarily to the technique implementing pedicle screws, the implants according to the present invention are not positioned in the vertebral pedicles but allow to solidarize directly the vertebral bodies between them. The device is from the start more solid than the pedicle screws commonly used in the prior art. Furthermore the vertebral bodies being large, in the range of 4×5×3 cm, the risk of an extracorporeal way is very limited compared to the vertebral pedicles that are in the rage of 1×0.8 cm and are quite difficult to identify even with efficient imaging techniques.

The present invention thus proposes also a new method for the fixing of at least two adjacent bone elements, as an instance two adjacent vertebrae, with no risk of false way and with no particular technical difficulty for the surgeon. This method allows also a considerable time gain in the case of the stabilization of more than two adjacent bone elements such as several vertebral levels. Moreover this new surgical implant which once set up forms a screw, is placed directly in the bone element, with no staple nor nail, thus an arthrodesis operation as en example can be realized with a closed spine between the nerve bundles and without damaging the nerves.

In the present invention, the terms in quotation marks are used to describe the new surgical implant, the new method for the fixing implementing it and the elements constituting it. They are used in both the plural as in the singular.

By «patient» is meant a human being or an animal whose symptoms or pathology require the intervention of a surgeon in order to solidarize at least two bone elements between them. For example a patient is an individual suffering from a fracture of vertebra or presenting a scoliosis, a vertebral compressing etc. the proposed method in order to alleviate pain of said patient being the realization of an arthrodesis, that is to say the bone fusion between two vertebrae.

By «bone element» is meant anatomical bone elements requiring a surgical intervention of stabilization or reparation but also any implant that replaces for all or part an anatomical bone element with an implant made of metal or metal alloy, ceramic, polymers, or any other biocompatible material.

The invention is directed to a surgical implant for the fixing of at least two adjacent bone elements of a patient, said implant being constituted of a rod intended to be sealed by means of a sealing element in a drilling practised in the at least two adjacent bone elements, characterized in that said rod is curved and hollow in order to form an open channel at the level of one of the ends and presenting at least one gap in such a way to allow the sealing element when injected within said channel through the open end to flow out outside the rod in contact with the bone elements to seal.

By «rod» is meant a solid element, preferentially of a cylindrical shape and which constitutes the body of the implant according to the invention.

By «curve» is meant a shape describing or comprising a plane arc portion or in three dimensions, not necessarily regular. The rod can be of a regular or mixed curve. When it is regular, the rod presents a regular radius of curvature, that is to say it corresponds to a circular arc regular on its whole length. We will then talk about a regular "curvature" or "arc of curvature". When it is mixed the rod presents a straight part and at least one curved part without the rod necessarily having symmetry. In some forms of achievement, the mixed rod may present two, three or more curved parts. We will then talk about mixed "curvature" or "arc of curvature".

By «hollow», one understands that the rod comprises on all or part of its length a drilling in the longitudinal direction so as to form a channel, said channel being open on one of the ends of the rod (in order to be able to introduce a sealing element by this open end). According to a particular embodiment, the channel is open at the level of the so-called "rear" or "distal" end of the rod, the other end, called "front" or "proximal" end being full and being able to present a pointed shape intended for facilitating the rod penetration within the bone elements. According to another particular embodiment, the channel can also be opened at the level of the proximal end of the rod in order to allow the flow out of the sealing element at this level as well.

By "gap(s)", according to a particular embodiment, is meant openings or windows practised on all or part of the rod which allow the channel formed within the rod to communicate with the outside of the rod. According to another embodiment of the invention, one understands one or several longitudinal slits that can extend on all or part of the rod. In practise, any sealing element injected within the channel will be able to flow out and spread out outside the rod in direct contact with the bone elements to seal. According to the nature of the bone elements to seal, the arrangement of the gaps could be adapted according to the general knowledge of a person skilled in the art.

The invention is also directed to a surgical implant, furthermore characterized in that said at least one gap consists of a plurality of openings distributed along the rod.

The surgical implant according to the invention is particularly adapted when said bone elements are vertebrae.

In a stripped version of the invention, the rod presents itself as a regular cylinder.

In another aspect of the invention, the rod can include an anchoring element present on all or part of the length of the rod and protruding in direction of the bone element.

In an embodiment of the invention, at least one of the anchoring elements is a thread. Said thread can be realized according to different profiles, especially round or sharp according to whether one searches an anchoring by support on the bone element or by insertion in this one.

According to a specific embodiment, the at least one thread is not of a constant height on its whole length. Thus the thread height emerging from the opening can be variable. An important height allowing to ensure an anchoring in a more friable bone element and a less important height allowing an anchoring in a harder bone tissue. The invention could also be realized with an absence of thread on certain parts of the rod in particular those that will be surrounded by a zone of non-bone tissues once the implant is installed. According to another additional characteristic the thread presents on its walls some elements such as strips or pins, eventually cleavable, aiming at anchoring said thread in the bone with no possibility of return unless being constrained there by a movement exerted by the surgeon with the couple necessary to fold them or to break them.

The shape of the rod determines the shape of the implant, thus in a particular embodiment the rod is curved and the surgical implant once installed is also curved. In a specific embodiment the rod is curved in different planes. According to an additional characteristic the shape of the surgical implant according to the invention is curved. According to another additional characteristic the shape of the surgical implant is mixed, that is to say that it presents one or several straight part(s) and one or several curved part(s).

According to an embodiment, the implant according to the invention is characterized in that said rod includes at least one curved part with a developed length ranging between 35 mm and 110 mm that will describe an arc with a radius typically ranging between 60 mm to 150 mm, preferentially a developed length ranging between 70 mm and 90 mm that will describe an arc with a radius typically ranging between 60 mm and 120 mm.

The present invention is also directed to a surgical implant characterized in that the rod includes at least a curved part.

The materials used for the realization of the surgical implant according to the invention are biocompatible solid materials for example a metal or a metal alloy, particularly titanium or titanium based alloys and/or steel or the steel based alloys, ceramics for medical use, the polymeric materials for medical use, said materials being considered alone or in combination. According to an additional characteristic the rod and is made of metal or of a metal based alloy. In another embodiment, the rod is made out of different biocompatible materials in order to present different properties according to its parts, especially of flexibility. Of course in specific embodiments it can be considered different surface treatments of the rod in order to ensure for example the biocompatibility, the cutting edge, the spring effect, the sliding or on the contrary the adherence of such or such of theses elements.

When the rod is made out of a rigid material, the surgeon must practise a drilling within the bone elements to be assembled whose curvature is identical to the one of the rod. When the rod is made out of a solid but flexible material, the rod can potentially be adapted to any curvature of the drilling realized by the surgeon according to predefined parameters. Thus according to an additional characteristic the rod is made out of one or several biocompatible(s) and flexible(s) material(s). The rod can in particular have the shape of a nail.

The present invention concerns also a surgical implant, characterized in that the rod is realized in one or more biocompatible materials that are flexible.

Generally and whatever the shape of the implant according to the invention is it can be considered to realize only some parts of the rod in a flexible material. For example the flexible parts could be envisaged to be positioned outside the bone elements to assemble, as an example two vertebrae in order to form a kind of hinge and to preserve certain flexibility at the implant. The present invention concerns also a surgical implant, characterized in that only some parts of the rod are flexible.

The simplicity of this surgical implant makes it particularly adaptable for the morphology of the adjacent bone element to fix between them. In fact it is easy to produce "customized" surgical implants with a slightly curved shape, having a symmetry or not compared to said curve, etc. All the forms are authorized in the present invention according to the zone to be implanted. For an implantation at the vertebral level, one will privilege for example a surgical implant with a curved shape in order to be adapted to the morphology of the vertebrae and to their articulation. The curvature is then determined according to the morphology of the bone elements to solidarize. The curvature of the implant according to the invention will not be necessarily planar and will be able to present torsions.

Typically for an adult patient, the rod has a diameter of ranging between 3 and 9 mm, preferentially around 6 mm. According to a more preferential embodiment of the invention perfectly adapted to the solidarization of two vertebrae for an adult patient the rod is of a curved shape in a plane, of a developed length of 70 mm describing an arc of 44.6° and with a constant radius equal to 90 mm.

The rod according to the invention presents as a characteristic to be hollow and includes in its centre a channel having a section of a diameter ranging between 2 and 8 mm, preferentially around 3 mm. As it will be more detailed below, this section is advantageously chosen by a person skilled in the art according to, in particular, the nature of the sealing element that will be used.

The present invention concerns also a surgical implant characterized in that the channel of the rod has a section with a diameter ranging between 2 and 8 mm, preferentially around 3 mm.

In the same way, the gaps can appear under a shape that is circular, oval, square, rectangular, etc. As a non-restrictive example, it will be described here gaps of a circular shape. In view of the described dimensions, a person skilled in the art will be able to deduce without difficulty the equivalent surface of theses gaps in the case where the shape differs. According to a particular mode, the circular gaps present a diameter ranging from 0.5 and 5 mm. In a particular embodiment, the gaps have a same diameter. According to another embodiment, the gaps can present along the rod different diameters, this in order to control the quantity of sealing element that will be able to flow out from the rod in function of the positioning of the latter within the bone elements to seal.

The present invention concerns also a surgical implant characterized in that the gaps have a diameter ranging between 0.5 and 5 mm.

In practise, the gaps are advantageously positioned along the rod particularly in function of the nature of the elements to seal, of the nature of the sealing element, etc. As a non-restrictive example, two particular embodiments are described below. According to an embodiment, the rod presents gaps on one, the other or both ends. According to another embodiment, the rod presents gaps on its whole length.

In a general manner, it can be considered that the respective diameters of the section of the channel and of the gaps will be mainly determined in function of the sealing elements that will be used. As an illustration, more the sealing element will be fluid and homogeneous, more these two diameters could be of a small size. In contrast, more the sealing element will be heterogeneous or viscous, more these two diameters will have to be of big size to allow a sufficient flow of the sealing element. Based on his general knowledge, a person skilled in the art will not have any problem to adapt these two diameters to the nature of the sealing element as it will arise from the examples below.

By «sealing element», it must be understood any material known by a person skilled in the art as able to be used in bone reconstruction or known to promote bone integration and/or bone growth.

The sealing element can be natural or synthetic such as, with no limitation to, auto-grafted osseous matter, hydroxyapatite-collagen, demineralized bone matrix (DBM in the English nomenclature for Demineralized Bone Matrix), a porous synthetic osseous substitute, an osteoinductive protein or a bone morphogenic protein (BMP in the English nomenclature for Bone Morphogenic Protein), an acrylic cement, or a combination of these elements. For clarity purposes it will be thereafter referred to a sealing element consisting of acrylic cement as opposed to an osseous substitute.

According to a first particular embodiment of the invention, acrylic cement can be used. Said cement generally consists of a chemical body formed by two principal polymer components such as for example the methylmethacrylate (MMA) and the polymethylmethacrylate (PMMA) whose polymerization allows the fixing of an implant. By way of an example, it can be quoted cements PALACOS®.

Within the context of this first particular mode, it should be noted that acrylic cements have the property to be injected under a relatively homogeneous, liquid or fluid form. Thanks to this property, the section of the channel and the diameter of the gaps on both ends can be reduced.

This last point illustrates a first alternative of arrangement of the gaps. The nature itself of the cement used involves avoiding any contact with the spaces between the bones to seal. It thus appears here an embodiment of the invention for which a person skilled in the art will be able to determine the arrangement of the gaps according to the nature of the sealing element and of the bone parts to seal.

According to a second particular embodiment of the invention, osseous cells or an osteoinductive protein can be used. By way of an example, it can be quoted the INDUCTOS® products.

In the context of this second particular mode, it should be noted that the osseous substitutes are generally presented in a less homogeneous and more viscous form than acrylic cement. A person skilled in the art will be able to adapt the channel section and the gaps section to this viscosity.

This more important viscosity will make it possible to distribute the gaps on the whole rod.

This last points illustrates a second alternative of gaps arrangement. The nature itself of the bone substitutes used does not imply avoiding any contact with the spaces between the bones to seal (even on the contrary). It appears also here an embodiment of the invention for which a person skilled in the art will be able to determine the arrangement of the gaps according to the nature of the sealing element and of the bone parts to seal.

According to a specific embodiment, the implant according to the invention presents at least one hooking device allowing the installation and the withdrawal of said rod by the surgeon using adapted ancillaries. According to a privileged embodiment the hooking device is located on a part of the end of the rod not inserted in the bone element. The hooking device can consist of any means known by a person skilled in the art, such as for example a threading, a hook, a ring, a notch, a flat, a magnet, a relief, a print, a withdrawal, a boring.

The invention proposes also a method for the fixing of at least two adjacent bone elements, implementing the surgical implant according to the invention, consisting in:

to practise with a drilling tool a drilling having the characteristics defined by the surgeon in function of the bone elements to solidarize, then to insert the rod in the drilling thus practised with an installation tool, then to inject within the channel intended for this purpose in the rod a sealing element that will come to flow out through the gaps practised on the whole or part of the rod so as to come in direct contact with the bone elements to seal.

The present invention according to a particular embodiment is directed to a process for the fixing of at least two adjacent vertebrae that implements a surgical implant as described above, said process consisting in:

to practise with a drilling tool a drilling having the characteristics defined by the surgeon in function of the vertebrae to solidarize, then to insert the rod in the drilling thus practised with an installation tool under medical radioscopy, then to inject within the channel intended for this purpose in the rod a sealing element that will come to flow out through the gaps practised on the whole or part of the rod.

When the surgeon judges it applicable in function of the bone elements to assemble and of the material constituting the rod, it can be envisaged to use a drilling and installation tool that employs the rod of the surgical implant presenting a pointed distal end as a drilling head. In this mode of realization there is no preliminary stage of drilling when the method according to the invention is applied.

The above-mentioned characteristics of the invention, as well as others, will more clearly appear with the reading of the following description of an example of realization, said description referring to the attached figures, among which:

Figure 4:
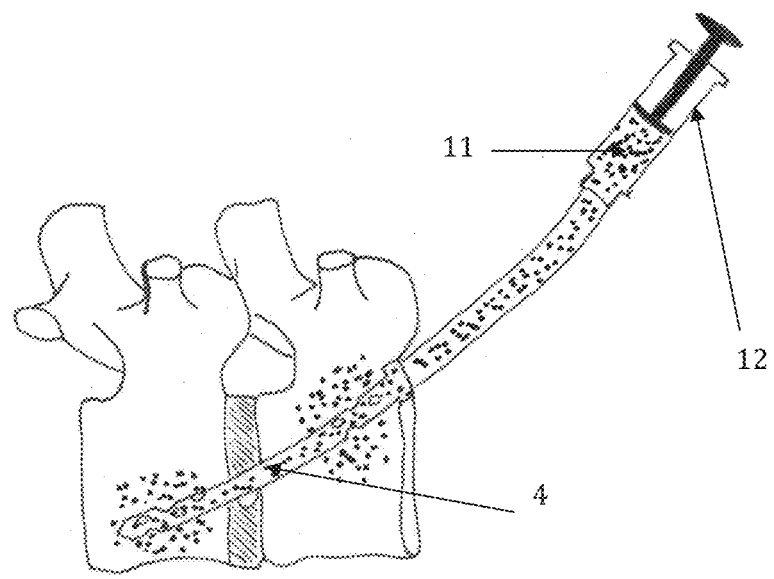

FIG. 4 represents the injection of the sealing element (8) through the open end (6) of the rod (4), said sealing element coming to flow out through the gaps (7) directly in contact with the adjacent vertebrae (2, 3). This example of installation of an implant according to the invention describes the solidarization of two adjacent vertebrae (2, 3) by means of a surgical implant (1) such as described above and the use of acrylic cement as a sealing element. The embodiment illustrated on FIG. 1 reveals a rod (4) of a curved shape with a regular arc of curvature.

Figure 1:
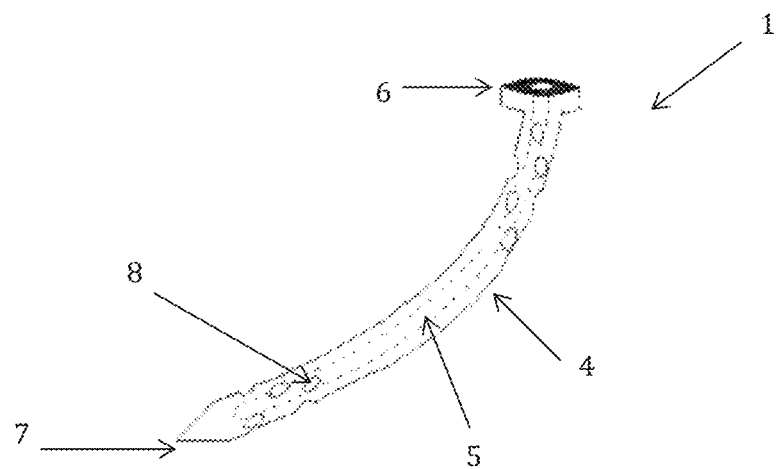
FIG. 1 represents a view of the rod (4) constituting the surgical implant (1) according to the invention.

More particularly, it is represented on FIG. 1 an implant (1) according to the invention composed of a rod (4) curved and hollow so as to form in its centre a channel (5) opened on the level of the distal end (6) of the rod (4). In this embodiment, the proximal end (7) is full and appears under the shape of a point. The represented rod (4) comprises in this embodiment adapted to the use of acrylic cement several gaps (8) in communication with the channel (5) distributed nearby the ends (6, 7) of the rod (4).

Figure 2:
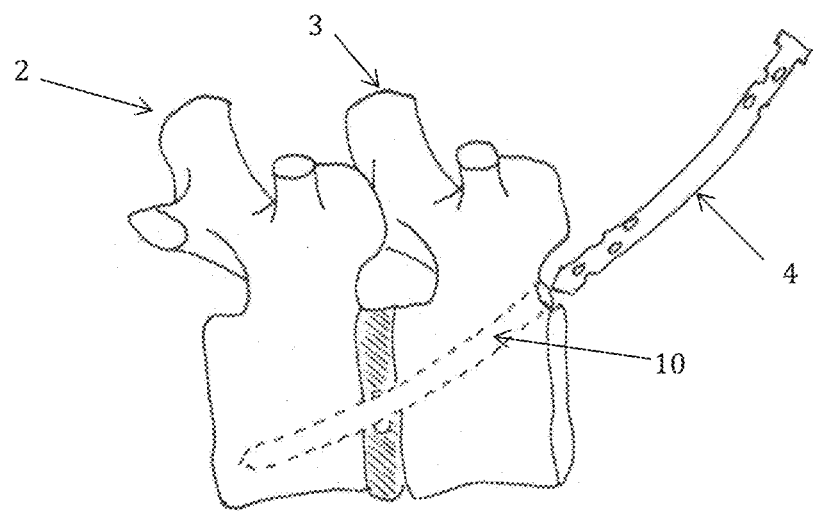
FIG. 2 represents a view or the rod (4) constituting the surgical implant (1) at the time it will be inserted in the drilling (5) practised within two adjacent vertebrae (2, 3)

FIG. 2 illustrates the rod (4) at the time it will be inserted within a drilling (10) previously realized by the surgeon. The advantage of the curved shape of the rod (4) comes out clearly from this figure where one can see the facility of installation of the implant.

In practise, the rod (4) can be inserted using a drilling and installation tool within two adjacent bone elements, here two vertebrae (tool not represented).

Figure 3:
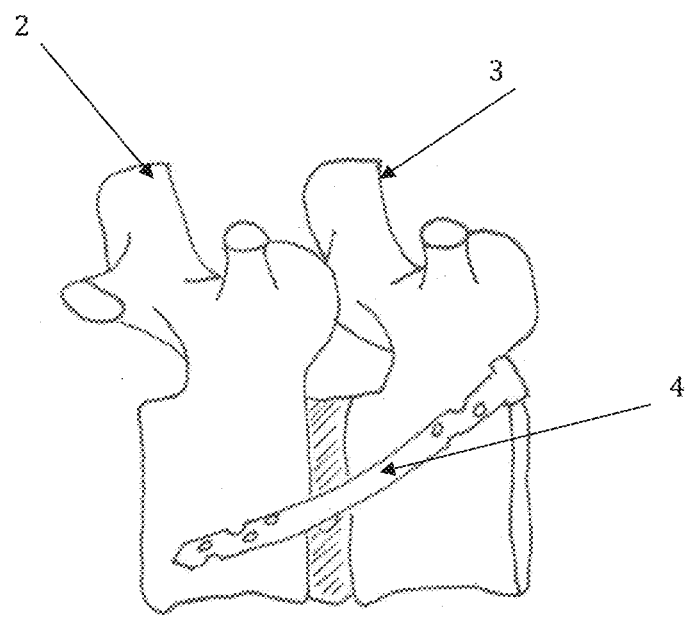
FIG. 3 represents the surgical implant (1) according to the invention, that is to say a rod (4) once inserted between two adjacent vertebrae (2, 3)

FIG. 3 shows the rod (4) once positioned within the two vertebral bodies (2, 3) to solidarize. As it comes out clearly from this figure, this rod (4) presents gaps (8) advantageously distributed on the level of the two ends so as to allow the cement to enter only in contact with the bone parts of the vertebrae (2, 3) but to avoid any contact at the level of the intervertebral spaces. This aspect is of a particular interest in the context of the use of acrylic cement as it has been described above. The opened end (6) is advantageously placed in order to allow its access very easily so as to facilitate the injection of cement by the surgeon.

FIG. 4 shows the surgical implant (1) in its final position within two adjacent vertebral bodies (2, 3) in our example. The cement (11) is then injected through a syringe (12) or any equivalent device directly within the channel (5) formed in the rod (4). This last will then flow out of the rod (4) through the gaps (8) directly in contact with the vertebrae (2, 3). In addition to the fact of solidarizing the implant (1) within the vertebrae, this cement flow will make it possible to come to fill the osseous spans of the vertebrae (2, 3) and thus to avoid the problems or complications linked to the pseudoarthrosis phenomenon.

According to an additional characteristic the surgical implant (1) can present a hooking device so as the surgeon can easily proceed to its installation and its withdrawal. This hooking point is ideally located on the level of the proximal end (7) of the surgical implant (1) that is to say on the level of the insertion point of the rod (4) in the first bone element. The withdrawal or uninstallation of the surgical implant (1) is made proceeding with the same operations than the installation but in the reverse order.

This method if particularly adapted to the fixing of several adjacent vertebrae in a patient presenting a lumber problem requiring the intervention of a surgeon because it allows to avoid the insertion of pedicle screws according to the techniques currently used, what is less invasive and limits largely the side effects linked to the operation of vertebrae fixing. Moreover, the operation can be considered with a closed spine under radioscopy control, while passing between the nerve bundles and without injuring the nerves.

As a first step a drilling is made with a first drilling tool. Then a setting tool is used in order to place the rod forming the implant from the cortical through the smooth part of the first vertebral body and finally towards the second vertebral body to be fixed. As a second step, the sealing element is injected within the channel of the rod on the level of the proximal end of the latter. The liquid will then come to fill the channel, and by simple effect of pressure, come to flow out through the gaps skilfully distributed for this purpose outside the rod in contact with the bone elements to seal.

The present invention relates also to cases or kits containing the material necessary to the implementation of the above-described method.

According to a first embodiment, the present invention concerns cases or kits containing a surgical implant in one of the above-detailed embodiments.

The present invention concerns also a kit containing a surgical implant according to the description above.

According to a second embodiment, the present invention concerns cases or kits containing a surgical implant in one of the embodiments detailed above and a drilling tool.

According to a third embodiment, the present invention is directed to cases or kits containing a surgical implant according to one of the embodiments detailed above, a drilling tool and an installation tool for the rod; these two tools forming an ancillary devices kit.

In a preferred embodiment the case or kit includes a curve shaped surgical implant and an ancillary devices kit.

The invention claimed is:

1. Surgical implant for fixing at least two adjacent bone elements of a patient, said implant comprising a rod and a homogeneous sealing element, the rod being configured to be sealed by the sealing element in a drilling made in the at least two adjacent bone elements,
   wherein said rod is a singular element which is curved in a relaxed state of the rod, is hollow in order to form a channel opened at one open end of the rod, and includes a plurality of gaps configured to allow the sealing element, when the sealing element is injected within said channel through the open end, to flow out outside the rod in contact with the bone elements to seal, and
   wherein the plurality of gaps are more densely distributed at opposite end portions of the rod.

2. Surgical implant according to claim 1, wherein said plurality of gaps comprises a plurality of openings distributed along the rod.

3. Surgical implant according to claim 1, wherein the rod is realized in one or several biocompatible materials that are flexible.

4. Surgical implant according to claim 1, wherein the rod is flexible at only some parts of the rod.

5. Surgical implant according to claim 1, wherein the channel has a section with a diameter ranging between 2 and 8 mm.

6. Surgical implant according to claim 1, wherein each gap of the plurality of gaps has a diameter ranging between 0.5 and 5 mm.

7. Kit including a surgical implant according to claim 1.

8. Method of using a surgical implant for fixing at least two adjacent bone elements of a patient, said implant comprising a rod which is a singular element which is curved and hollow in a relaxed state of the rod, wherein the rod includes a channel with an open end at an end of the rod, and a plurality of gaps extending through a wall of the rod, wherein the plurality of gaps are more densely distributed at opposite end portions of the rod, the method comprising:
   inserting the rod into a drilling made in the at least two adjacent bone elements; and
   injecting a homogeneous and fluid sealing element within the open end of the channel, the fluid sealing element flowing inside the rod and from inside the rod through the plurality of gaps to outside the rod to contact the bone elements to form a seal.

9. Method according to claim 8, wherein said plurality of gaps comprises a plurality of openings distributed along the rod.

10. Method according to claim 8, wherein the rod is realized in one or several biocompatible materials that are flexible.

11. Method according to claim 8, wherein the rod is flexible at only some parts of the rod.

12. Method according to claim 8, wherein the channel and has a section with a diameter ranging between 2 and 8 mm.

13. Method according to claim 8, wherein each gap of the plurality of gaps has a diameter ranging between 0.5 and 5 mm.

* * * * *